(12) United States Patent
Gidekel et al.

(10) Patent No.: US 8,357,407 B2
(45) Date of Patent: Jan. 22, 2013

(54) AGENT FOR CUTANEOUS PHOTOPROTECTION AGAINST UVA/UVB RAYS

(76) Inventors: Manuel Gidekel, Santiago (CL); Ramon Lucas Molina Carlevarino, Santiago (CL); Gustavo Cabrera Barjas, Santiago (CL); Carlos Sunkel Letelier, Madrid (ES); Ana Gutierrez Moraga, Santiago (CL); Juan Pablo Pivel Ranieri, Tres Cantos (ES); Juan Manuel Ferrer Cuesta, Tres Cantos (ES); Maria Teresa Sanz Berzosa, Tres Cantos (ES)

( * ) Notice: Subject to any disclaimer, the term of this patent is extended or adjusted under 35 U.S.C. 154(b) by 0 days.

(21) Appl. No.: 12/736,727

(22) PCT Filed: Jan. 30, 2009

(86) PCT No.: PCT/ES2009/000050
§ 371 (c)(1),
(2), (4) Date: Jan. 24, 2011

(87) PCT Pub. No.: WO2010/086464
PCT Pub. Date: Aug. 5, 2010

(65) Prior Publication Data
US 2011/0195034 A1    Aug. 11, 2011

(51) Int. Cl.
*A61K 36/899* (2006.01)
*A61K 36/00* (2006.01)
*A61K 8/00* (2006.01)
*A61K 8/18* (2006.01)
*A61Q 17/04* (2006.01)

(52) U.S. Cl. .................. 424/750; 424/725; 424/59

(58) Field of Classification Search .................. None
See application file for complete search history.

(56) References Cited

FOREIGN PATENT DOCUMENTS
WO    WO2009064480    9/2009

OTHER PUBLICATIONS

Bravo et al. "Characterization of antifreeze activity in Antarctic plants". Journal of Experimental Botany, vol. 56, No. 414 (Apr. 2005) pp. 1189-1196.*
Zuniga et al. "Non-Structural Carbohydrates in *Deschampsia antarctica* Desv. From South Shetland Islands, Maritime Antarctic". Environmental and Experimental Botany, vol. 36, No. 4 (1996) pp. 393-399.*
Pereira, B.K. et al. 2009. Protective effects of three extracts from Antarctic plants . . . J. Photochem, Photobiol.B: Biology.vol. 26. pp. 117-129.

* cited by examiner

*Primary Examiner* — Chris R Tate
*Assistant Examiner* — Russell Fiebig
(74) *Attorney, Agent, or Firm* — John H. Dodds

(57) ABSTRACT

This invention describes an agent for cutaneous photoprotection against UVA (I and II) and UVB radiation that contains an aqueous extract obtained from a plant in the Gramineae family from the Antarctic Continent (*Deschampsia Antarctica*), which presents both antioxidant and dissipation of excess UV radiation properties.

4 Claims, 1 Drawing Sheet

AGENT FOR CUTANEOUS PHOTOPROTECTION AGAINST UVA/UVB RAYS

TECHNICAL FIELD

This invention relates to the field of human skin protection against the harmful effects of UVA (I and II), UVB and visible light solar radiations.

BACKGROUND ART

The sun is our principle source of energy, manifesting itself mainly in the form of light and heat, issuing electromagnetic radiation that travels through space in the form of waves and particles. The waves are described by their frequency (v) or their wavelength (λ). The following table shows the solar electromagnetic radiation spectrum:

TABLE 1

Solar Radiation Spectrum

| Solar Radiation | Wavelength |
| --- | --- |
| Cosmic Rays | 0.005 Å |
| Gamma Rays | 0.005-1.4 Å |
| X-Rays | 0.1-100 Å |
| Ultraviolet C (UVC) | 200 nm-280 nm |
| Ultraviolet B (UCB) | 280-320 nm |
| Ultraviolet A I (UVA I) | 320-340 nm |
| Ultraviolet A II (UVA II) | 340-400 nm |
| Visible Light | 400-740 nm |
| Near-Infrared | 740 nm-1,500 nm |
| Mid-Infrared | 1,500-5,600 nm |
| Far-Infrared | 5,600-10,500 nm |
| Microwaves and Radio Waves | >10,600 nm |

Not all solar radiations reach earth since part of these are reflected, absorbed or dispersed because the Earth is protected by atmospheric gas layers that filter and attenuate the solar radiations. Only radiation from 290 to 1,800 nm (UVB, UVA (I and II), visible and near infrared) reach the surface of the earth. Of this range, UVB and UVA (I and II) are the ones that reach the surface the least as they are filtered by the ozone layer, but they are the ones that most affect the biosphere, including humans. On the other hand, the harmful effects of solar radiation is attracting more and more attention, particularly because of the of the ozone layer depletion phenomenon, which reduces the filtering effect on solar radiation (see *Ozone Depletion and Human Health Effects*, by M. J. Molina and Luisa T. Milina, Environmental Medicine; L. Möller Ed. Sep. 24, 2002 ENVIMED).

Figure 1:
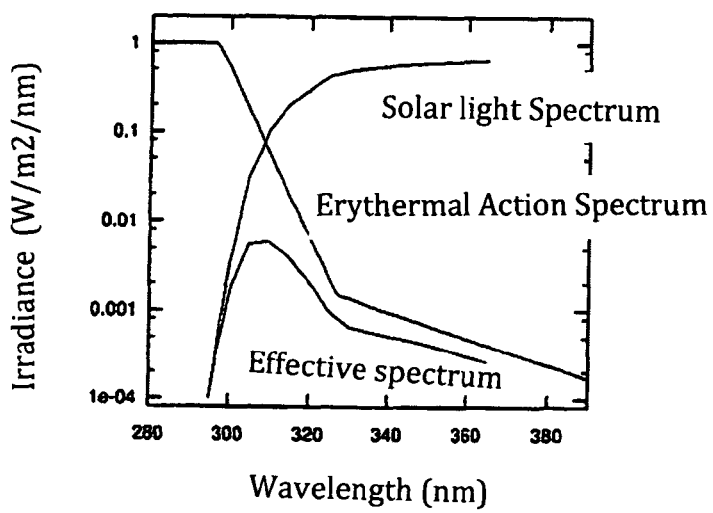

Overexposure to UVB radiation produces harmful effects on the skin in the short-term, producing erythemas, which is the well known inflammation process with reddening of the skin. Overexposure to UVA, on the other hand, produces harmful effects in the longer term. We may observe a graph that has been made public showing the solar spectrum reaching earth in terms of wavelength, the erythemal action spectrum, and the relationship between them in FIG. 1. This graph shows what has been indicated above, that is, that erythema is produced mainly by the incidence of UVB radiation on the skin, whereas UVA I and II (320-400 nm) does not produce such a skin reaction. UVA I and II, however, produce other long-term effects that are much more harmful, such as photoaging and photocarcinogenesis (see Photocarcinogenesis: UVA vs UVB Radiation, by Fr. R. de Grujil, Skin Pharmacol. Appl. Physiol. 2002; 15:316-320).

The principal differences between the harmful effects of UVB and UVA radiation on the skin are presented in the following Table:

TABLE 2

Comparative Effects of UVB and UVA Radiation

| Radiation | Energy | Skin Penetration | Damage | Photodynamic Action |
| --- | --- | --- | --- | --- |
| UVB | +++ | Little | Direct | — |
| UVA | + | Substantial | Direct and Indirect | Substantial |

The skin has chromophores capable of absorbing UVA radiation, primarily melanin and urocanic acid, in addition to nucleic acids and protein aromatic residues.

Because of its greater skin penetration, UVA radiation has a longer term effect on skin degeneration in view of its higher photodynamic action. The photodynamic action produced by UVA radiation is a result of the reaction of the UVA (I and II) energy (hv) with photosensitizers in the skin or the environment in the presence of oxygen in the air. This produces reactive oxygen species (ROS), which are known as free radicals and singlet oxygen (see "Sunscreen enhancement of UV-induced reactive oxygen species in the skin", Ferry M. Hanson et al., Free Radical Biology & Medicine 41 (2006) 1205-1212). Free radicals are, by definition, reactive chemical species that contain non-paired electrons in their respective orbitals, and that may be neutral, negatively or positively charged. They are highly unstable and therefore tend to react, altering the cellular components. They are therefore associated with photoaging, melanoma and skin cancer, among other diseases (see "Free Radicals in Cutaneous Biology", J. Invest. Dermatol. 102:671-675, 1994 and "Cutaneous Photodamage, Oxidative Stress and Topical Antioxidant Protection", J. Am. Acad. Dermatol. 2003; 48:1-19, Tedesco A C et al, 1997).

There are many studies on chemical and physical filters focused on avoiding these harmful effects on the skin, such as "Photoprotection" by P. Kullavanijaya and H. W. Lim, J. Am. Acad. Dermatol. 2005; 52:937-58 and "Ultraviolet Radiation Screening Compounds", Biol. Rev. (1999), 74, pages 311-345, whose purpose is topical photoprotection by means of substances that absorb and filter UVB and UVA radiation (chemical filters); that inactivate or destroy the reactive oxygen species (free radicals and singlet oxygen) that are produced in the skin by means of antioxidants; or that reflect the radiation by dispersion with physical filters such as $TiO_2$ or ZnO. In fact, it has been make known that there are vegetable extracts with antioxidant properties able to offset the oxidative effects induced by $TiO_2$ (see "Plypodium Leucotomos Extract Inhibits Trans-Urocanic Acid Photoisomerization and Photodecomposition", Journal of Photochemistry and Photobiology B: Biology 82 (2006) 173-179).

On the other hand, the effect of UVB and UVA ultraviolet radiation also affects plants (see Journal of Photochemistry and Photobiology B: Biology, Volume 76, Issues 1-3, Oct. 25, 2004, Pages 61-68), with plants having their own defense mechanisms, as not only men naturally generate photoprotective substances, such as melanin. Plants also generate their own defenses, such as *Deschampsia Antarctica*, which grows under very low temperatures with spells of very high solar radiation. This has lead it to develop effective defense mechanisms to cope with these extreme conditions. It is able to dissipate the reactive oxygen species (ROS) by developing an elevated antioxidant capacity, along with a large capacity to process the excess UV radiation non-radiatively as heat in small quantities. This plant is peculiar in that it grows in the Antarctic Continent and tolerates the extreme conditions in its habitat without problems. It is able to stay green throughout the year, even under ice and snow during the Antarctic winter, being one of the few plants able to tolerate such extreme climatic conditions. (see "*The Role of Photochemical Quenching and Antioxidants in Photoprotection of Deschampsia Antarctica*", in Functional Plant Biology, 2004, 31, 731-741).

There is today a large necessity to obtain products for durable skin protection against the adverse effects produced by UVA and UVB radiation. Although it is known that an antioxidant neutralizes the photodynamic action produced by reactive oxygen species (ROS), it is necessary to detect which antioxidants are adequate and to verify their effects, since not all are beneficial, as they can produce chain propagation and other even worse consequences. Various biological factors, such as skin tropism, also have to be considered.

SUMMARY OF INVENTION

This invention is based on the use of the antioxidant and excess UV radiation dissipative properties of an aqueous extract of a plant belonging to the Gramineae family, *Deschampsia Antarctica* (DA), to obtain a photoprotection agent with these characteristics. It has been observed that an aqueous extract with these characteristics, hereinafter designated as AEDA (Aqueous Extract of *Deschampsia Antarctica*) has photoprotection properties against UVB and UVA (I and II) radiation, since:

i) On the one hand, the antioxidants it contains offset the negative effects produced by the formation of free radicals, which are produced mainly by the UVA II radiation as a result of its photodynamic action when it irradiates the skin in the presence of photosensitizers and oxygen.

ii) On the other hand, it is important to note that both melanin, the most important cutaneous cromophore, and DA are able to eliminate excess radiant energy, although using different mechanisms. In the case of melanin, the excess radiant energy is eliminated in the form of small pulses of heat ("ultraphase internal conversion"), and in the case of DA "Photo Chemical Quenching" is used, which in any case is able to block biological photoinhibition.

This invention, in this technical field relating to the use of the antioxidant properties of certain plants and their possible application for photoprotection, considering that not all antioxidants are photoprotectors, refers to the antioxidant properties and dissipation of excess UV radiation characteristics of this plant to obtain an aqueous extract for use as a cutaneous photoprotector.

The AEDA under this invention may be extracted from the plant obtained from its native environment or from plants propagated in an artificial environment. The plant grows naturally in the Antarctic Continent, which is a territory subject to strict regulations for its protection, which make its exploitation, and therefore the harvesting there of *Deschampsia Antarctica* for commercial purposes impossible. It therefore becomes necessary to obtain it by artificial means outside of its natural habitat.

The *Deschampsia Antarctica* extract (AEDA) is obtained by a procedure previously established by the authors, which makes use of an aqueous method. This avoids the use of organic solvents, which present contamination problems and residues that are difficult to eliminate from the extract.

The AEDA so obtained may be used to obtain a cutaneous photoprotection agent for UVA (I and II) and UVB radiations.

This active photoprotection agent may be combined with conventional excipients and additives to obtain its formulation as a cream, gel or liquid in lotions, oils, suspensions or ointment for topical skin application.

The AEDA that was so obtained was tested to establish its physicochemical and pharmacological characteristics.

The following is a summary of these tests:

Thin layer Chromatography (TLC)

The TLC technique was utilized for the separation of the compounds that form part of a mixture (see Attachment 1). The AEDA that was obtained was spotted on a silica gel 60 $F_{254}$ plate (MERCK), using the following as solvents:

N-Hexane: Ethyl Acetate (50:50)

Ethyl Acetate: Methanol (80:20)

Ethyl Acetate: Formic Acid: Glacial Acetic Acid: Distilled Water (67:6.4:6.4:18.2)

The AEDA was subjected to a UV/VIS spectral analysis at 200-400 nm to determine the peak absorbency of the compounds with UV absorbing characteristics present in the AEDA. A SHIMADZU UV-160 photospectrometer was used for this purpose, with the samples diluted in ethanol until a visible reading in the spectrum was obtained.

Quantification of the AEDA Antioxidant Activity

Folin's colorimetric test was performed to measure the amount of polyphenols in the AEDA. This reaction is characteristic of those compounds with a hydroxyl group attached to the benzene ring. The Folin-Ciocalteau reagent changes from yellow to blue when phenols are present. The intensity of the blue is measured by a spectrophotometer at a wavelength of 765 nm (see Attachment 3). The AEDA's antioxidant characteristics were evaluated by means of the ABTS colorimetric method, which is based on the progressive generation of stable radical $ABTS^+$ cations, whose presence is detected by the reduction in the system's absorbency at a wavelength of 734 nm (the wavelength at which this cation presents one of its maximum absorption peaks and degradation or chelation of the cation by its interaction with an antioxidant substance).

The quercetin index for the analyzed AEDA was determined to obtain an indicator for the phenolic compounds index, since this is a flavonoid with a double-bond between carbons 2 and 3, a free OH group in position 3 and a carbonyl group in position 4, which enhances the compound's antioxidant strength. A calibration curve with quercetin was prepared with concentrations ranging from 0.2 mg/ml to 0.8 mg/ml, to then measure the absorbency of the different AEDA's at a wavelength spectrum of 350 nm and a concentration of 0.5 mg/ml.

Aqueous AEDA HPLC Reference

An HPLC analysis with a UV detector was performed to obtain a reference for the compounds that might be present in the AEDA's that were obtained. A Shimadzu SPD-M10AVP diode array detector with an RP-18.5 μm 25 cm column was used for the HPLC, with a methanol:water mixture used as solvent, and with the samples run in a program with a 0.7-0.8 ml/min flow gradient.

Different tests were conducted with guinea pigs once the AEDA had been absorbed, to verify its photoprotective effects against UVB and UVA (I and II) radiation in these rodents' skin:

Cellular Viability Study (Cellular Cycle) of the *Deschampsia Antarctica* (AEDA) Aqueous Extract A study of the cellular viability (cellular cycle) of the *Deschampsia Antarctica* (AEDA) aqueous extract was performed at a dosage of 10 mg/ml in the presence of ultraviolet light on HaCaT cells. The human HaCaT keratinocyte line was cultured in a DMEM medium with 10% fetal bovine serum.

TABLE 3

Extracts used in the Tests

| AEDA Identification | Starting Biological Material | Solvent Used |
|---|---|---|
| M2 | DA plant collected in the Antarctic Territory | 100% Deionized Water |

A control group (without AEDA) and a group with AEDA M2 was used for this first test, which was irradiated 4 hours after the start of the experiment with simulated solar ultraviolet radiation at a dosage of 9.75 J/cm2 UVA 0.75 J/cm2 UVB.

The incubation lasted 24 hours without additives. The cells were afterwards detached with trypsin, set with 60% ethanol and incubated in a buffer with propidium iodide, Triton X-100 and RNAse. The propidium iodide attaches to the DNA and emits fluorescence which is measured with a flow cytometer. The total number of cells and the percentage that is in the quiescent/senescent phase (G0/G1), in synthesis (S) or in mitosis (M/G2), as well as the cells in apoptosis (Sub-G0) was thereby determined. This approach made it possible to determine if the AEDA are toxic or mitogenic, and their ability to revert solar ultraviolet radiation damage.

To be able to compare the experiment and to obtain values that were easily understandable, the variation in the number of cells in relation to the control without additives was calculated. A total of 3,000 to 5,000 cells were evaluated and normalized to 100 in each experiment. Thus, if 41% of the cells were found to be in phase G0/G 1 and 39% in phase G2/S in the control without additives, the variations that were observed with AEDA were compared to this result for the control group.

The results that were obtained are shown in Table 4 below, with negative values indicating a decrease in the number of cells compared to the control group, and the positive values indicating an increase compared to the control group:

TABLE 4

Results of the Cell Viability - Cell Cycle Study

| | Control (% cells in each state) | | Without UV Light (% variation compared to the control group) | After irradiation with UV (% variation compared to the control group) |
|---|---|---|---|---|
| | Without UV | With UV | M2 | M2 |
| SubG0 | <1 | 43 | | 6 |
| G0/G1 | 41 | 39 | −30 | −13 |
| G2/S | 39 | 10 | 39 | 11 |

It can be seen that M2 increases the proliferation of the non-radiated cells, an increase which was also registered under radiation.

The repetition of this experiment showed a similar effect: a proliferative effect and resistance to apoptosis after UV radiation. It is important to note that in this new study, the cells were predominantly in the quiescent/senescent compared with the more proliferative state in the previous study (5% G2/S cells versus 39% in the previous study). The results may be seen in Table 5 below:

TABLE 5

| | Control (% cells in each state) | | Without UV Light (% variation compared to the control group) | After irradiation with UV (% variation compared to the control group) |
|---|---|---|---|---|
| | Without UV | With UV | M2 | M2 |
| SubG0 | 5 | 54 | −17 | −20 |
| G0/G1 | 81 | 39 | 3 | 26 |
| G2/S | 5 | 2 | −40 | 31 |

It may be concluded, averaging the results of both experiments, that M2 produced little variation in the number of cells in the G2/S phase and that, after irradiation with UV light, there is a 7% decrease in the number of cells in apoptosis with M2.

Effect of the Aqueous *Deschampsia Antarctica* (AEDA) Extract on Rat Skin under UVB Radiation a) A first test was conducted to assess the effect of UVB radiation on 3 male rats, administering 0.1 ml of a *Deschampia Antarctica* preparation at a concentration of 300 mg/ml once a day from Monday to Friday. The central area was compared to the peripheral area, so that each animal was its own control. After exposure to UVB (290-350 nm) following the method described by Zinder & Collaborators, and other authors, with the animals placed 8 cm from a 6*40 W ultraviolet UVC filtered light source emitting mainly at 313 nm in a range from 290 to 350 nm (considered as wide band), the erythema that was formed was subjectively evaluated with crosses, discriminating the peripheral area (untreated) from the central (treated) area and photographed 24 hours after exposure. The results were as follows:

| Location | R1 | R2 | R3 |
|---|---|---|---|
| Periphery | 4+ | 4+ | 4+ |
| Center | 1+ | 2+ | 1+ |

From these results it was possible to conclude that the AEDA at 300 mg/ml decreased the intensity of the erythema produced by the UVB radiation.

b) The effects of AEDA on the formation of a dermal erythema and the appearance of burned cells, designated as "sunburnt" cells due to the exposure of the rat skin to a strong source of 290-320 nm radiation, within the UVB light spectrum, was studied in a second test.

The results were compared with the effect of ferulic acid, which was used as a reference substance, and which is a very low toxicity antioxidant that is very widespread in the vegetable kingdom, protecting cellular membranes from lipid oxidation, and the cellular genome from mutagenesis and oxidative damage (3).

Materials and Methods 40 male rats weighing more than 20 grams were used. They were acclimatized to the location where the tests were carried out during 7 days after being received. The animals were placed in a room with controlled temperature (22° C.), relative humidity between 50% and 75%, filtered fresh air turnover approximately every 10 hours, and 12 h light/dark cycles (7:00-19:00 light, and 19:00 to 7:00 darkness). The animals were fed ad libitum with a standard rodent diet and running water during this period and during the experimental period.

TABLE 10

| Group | Treatment | UVB Exposure | Dosage | Method of Administration |
|---|---|---|---|---|
| 1 | Blank Vehicle | No | ... | |
| 2 | Positive Control Vehicle | Yes | ... | |
| 3 | *Deschampsia Antarctica* Extract (WDA) Aqueous Gel at 300 mg/ml* | Yes | 100 µl. on 2 × 2 cm | Topical |
| 4 | Ethanol Gel w/ Ferulic Acid 0.5%* | Yes | 100 µl. on 2 × 2 cm | Topical |

*Dissolved in distilled water (WDA) or ethanol (Ferulic) and suspended in an inert carbopol gel as vehicle.

The animals were randomly grouped in 4 experimental groups of 10 animals each, as presented in Table 10. The products to be tested were applied directly on the skin as a gel. The test was conducted following the method described by Winder et al. "A Study of Pharmacological Influences of Ultraviolet Erythema in Guinea Pigs". Arch. Int Pharmacodyn, 116: 261-292. 1958, and other authors such as Wendy, J et al. "The Local Antinociceptive and Topical Anti-inflammatory Effects of Propyl Gallate in Rodents". Br. J. Pharmacol, 58: 573-581. 1976, and Katiyar, S. K. et al. "Protective Effects of Silymarin Against Photocarcinogenesis in a Mouse Skin Model". J. Natl. Cancer Inst. 89: 556-65. 1997, with slight modifications.

The animals were shaved clean six days before the test to eliminate all traces of hair, leaving the skin on their backs completely bare.

A morning (10:00 h) and evening (20:00 h) dosage regime for the substance to be tested or for the standard commenced on the first day of the test on a randomized and blind basis lasting 3 days. On the third day, after applying the corresponding morning treatments, the animals were placed and secured in the equipment's exposure platform. The animals were then placed 8 cm from the 4*40 W ultraviolet light source emitting at a fundamental frequency of 313 nm and in a range from approximately 290 to 350 nm, with an anti-UVC filter.

The exposure was maintained until all animals received a total dosage of approximately 2.5 kJ/m2, with the irradiation dosis determined by means of an ultraviolet light detector. The backs of the animals were photographed 24 hours after the exposure, and the animals were sacrificed by cervical dislocation. The back skin was removed and a 2×2 cm fragment located under the area were the substance to be tested was applied was placed and maintained for 6 hours in a jar with 10% tamponated formalin, before initiating the paraffin inclusion process and preparation for the histological study.

The preparations were observed under an optical microscope and the epidermal-dermal space was photographed at ×100 magnification in 5 different locations for each preparation. A count of sunburnt cells was made for each photograph, considering cells as sunburnt if they had hypereosinophilic cytoplasm with small dark and irregular dense nuclei different than those of its neighbors.

The evaluation of the erythema was made on a positive/negative basis, obtaining the percentage of protected animals.

The number of hypereosinophilic cells with pyknotic nuclei (sunburnt) was counted in the photographic fields for each of the five different sectors in each histological preparation. The sum of the five counts was considered as the value for each animal. The average±s.e.m. for the individual results in each experimental group was then obtained, and the percentage change was calculated for the group that was exposed and treated with the substance to be tested compared to the control group, as well as to the non-exposed control group.

Results i) The aspect of the rat skins of the "Blank Vehicle" (Group 1) that was not exposed to UVB was completely normal and pinkish, and designated as Negative Erythema. A normal skin structure was observed in the histological preparation, consisting of the presence of a normal stratum corneum (fine), a thin stratum granulosum and a stratum spinosum a couple of cells deep, supported on a layer of basal cells (stratum basale) of functional keratinocytes perfectly ordered cells, grouped in a one cell deep layer that clearly and evidently delimits the separation between epidermis and dermis. The presence of cells compatible with the definition of "Sunburnt" was not observed in any of these preparations.

ii) All animals in the "Positive Control Vehicle" (Group 2) showed intense erythema 24 hours after exposure, accompanied with evident symptoms of inflammation, very intense at times, with variable areas of hematic extravasation that ranged from small petechiae to clearly hemorrhagic lesions. Profound alterations in the cellular structure of the epidermis, whose arrangement in layers was lost, were observed in the microphotographs. Neither the stratum granulosum nor the stratum spinosum could be identified.

The stratum basale was replaced by a group of pyknotic cells, among which a considerable number of "Sunburnt" cells were found.

iii) The treatment with ferulic acid 0.5% (Group 4) effectively protected the animals from erythema at 70%, with the skin presenting a rosy aspect compatible with normality. Despite this, the affected animals only evidenced small erythematous point and petechiae of little importance. The histological image shows that the UVB induced very small skin changes. The stratum basale separating the epidermis and the dermis was maintained almost integrally. The stratum granulosum and spinosum lost height and the stratum corneum appeared thicker. Although the number of sunburnt cells was small, numerous pyknotic nuclei are observed, indicating certain damage to the epidermal structure.

iv) Similarly, in the group treated with AEDA at 300 mg/ml (Group 3), a normal stratum basale is observed, with an almost normal stratum spinosum and a thickening of the stratum corneum. The number of sunburnt cells was very low. The backs of the animals did not present reddening so all animals were designated as with negative erythema. The photoprotector effect of AEDA at 300 mg/ml and of ferulic acid 0.5% on erythema induced by UVB radiation in rats is shown in Table 11. The results are expressed in terms of the presence (+) or absence (−) of erythema or its manifestations in the treated area. The term "protected" refers to those animals that do not show signs in the exposed area, or that, if they do appear, are of scarce importance; and the term "suppression" refers to a reduction in the intensity of the erythema and other manifestations compared to the Positive Control Vehicle where they appear (subjective criteria).

TABLE 11

| | Blank | Positive Control Vehicle | EDA 300 mg/ml | Ferulic Acid 0.5% |
|---|---|---|---|---|
| 1 | 0 | 38 | 2 | 10 |
| 2 | 0 | 30 | 8 | 0 |

TABLE 11-continued

|   | Blank | Positive Control Vehicle | EDA 300 mg/ml | Ferulic Acid 0.5% |
|---|---|---|---|---|
| 3 | 0 | 31 | 2 | 11 |
| 4 | 0 | 25 | 0 | 7 |
| 5 | 0 | 29 | 0 | 8 |
| 6 | 0 | 42 | 1 | 4 |
| 7 | 0 | 28 | 2 | 4 |
| 8 | 0 | 34 | 0 | 3 |
| 9 | 0 | 35 | 0 | 2 |
| 10 | 0 | 35 | 1 | 3 |
| Average ± S.E.M. | 0 | 32.7 ± 1.52 | 1.6 ± 0.72 | 5.2 ± 1.08 |
| % inhibition versus Positive Control Vehicle | | | 95.11%* | 84.1%* |

*p < 0.01 versus Vehicle

TABLE 12

|   | Blank | Positive Control Vehicle | EDA 300 mg/ml | Ferulic Acid 0.5% |
|---|---|---|---|---|
| 1 | − | + | − | + |
| 2 | − | + | − | − |
| 3 | − | + | − | + |
| 4 | − | + | − | − |
| 5 | − | + | − | + |
| 6 | − | + | − | −/+ |
| 7 | − | + | − | − |
| 8 | − | + | − | − |
| 9 | − | + | − | − |
| 10 | − | + | − | − |
| % Protected | − | + | 100%* | 70%* |
| % inhibition versus Positive Control Vehicle | | | 100% | 90% |

*p < 0.01 versus Vehicle

The statistical significance of the differences was evaluated by means of non-parametric tests, such as the Fisher Test or the $\chi^2$ (Chi Squared). Table 12 presents the presence of "Sunburnt" cells induced by UVB radiation in rats, with the results expressed in terms of the number of cells in the histological preparations in the treated areas.

Figure 2:
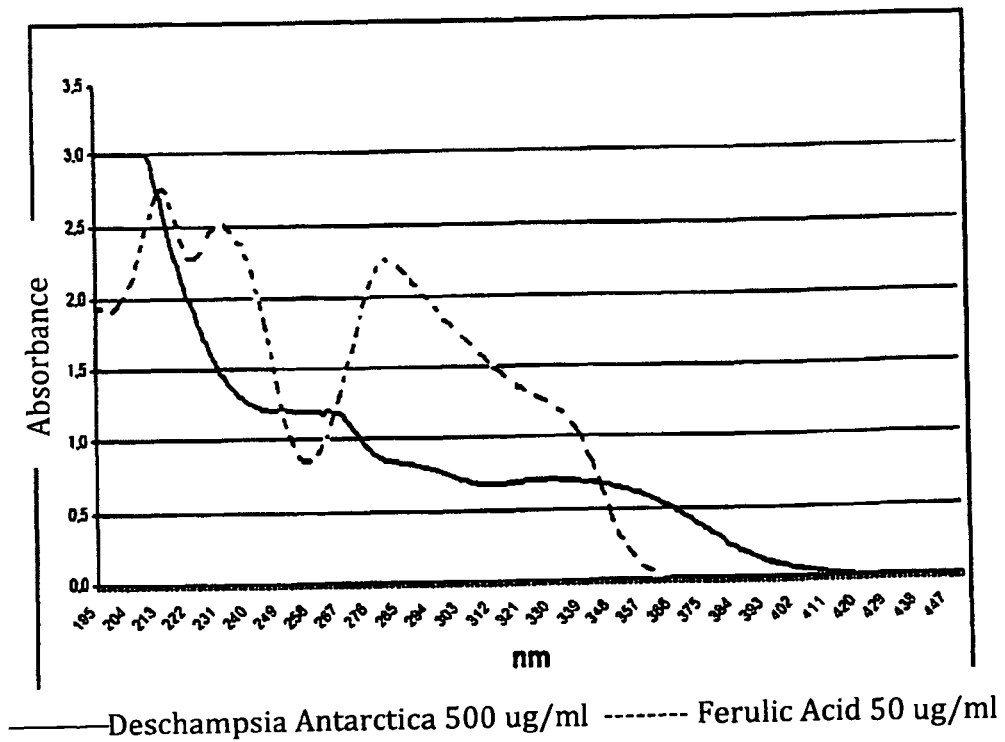

FIG. 2 shows the comparative spectral absorption of AEDA at 500 μg/ml with ferulic acid at 50 μg/ml. The AEDA absorption spectra show maximum absorption at wavelengths under 240 nm. In the band from approximately 250 nm to 350 nm. AEDA offers stable absorbency between 0.75 and 1.5 UA that blocks a significant amount of UVC, UVB and the more energetic portion of UVA light. Part of its effects may therefore be due to a screen effect that prevents the luminous radiation from reaching the skin.

Comparatively, ferulic acid shows three absorption peaks which may be seen in the Comparative FIG. 2. The first two are located before the UVC band, and the third appears above 285 nm and extends to almost 340 nm. This behavior is typical of the polyphenols present in numerous vegetals, which provide and an effective screen effect that protects plants from solar light. When comparing the concentrations required to reach similar absorbencies, it can be observed that ferulic acid develops its effective blocking ability at 50 μg/ml, whereas with AEDA, 500 μg/ml produce a block equivalent to 50% of that obtained with 50 μg/ml of ferulic acid. To produce similar blocking intensities, the necessary concentrations of AEDA must be 10 to 50 times higher than with ferulic acid.

To summarize, it may be stated that.
a) The topical application of AEDA at 300 mg/ml effectively reduces the erythema induced by UVB radiation.
b) AEDA applied topically at 300 mg/ml inhibits the appearance of sunburnt cells by 95.11%.
c) The strength of the Deschampsia prepared in this test is slightly better than that shown by ferulic acid at 0.5%
d) The concentration of Deschampsia Antarctica required to block UV has to be from 10 to 50 times larger than with ferulic acid.

The invention claimed is:

1. A photoprotection composition in the form of a cream, gel, oil, or lotion for cutaneous application, comprising an effective amount of an aqueous extract of *Deschampsia antarctica*, wherein the extract has cutaneous photoprotection properties against A or B forms of ultraviolet radiation.

2. The composition according to claim 1, wherein said extract is prepared by extracting *Deschampsia antarctica* plant material with 100% deionized water, wherein said *Deschampsia antarctica* plant material is obtained from its native environment or propagated in an artificial environment, and wherein said extract comprises polyphenol compounds.

3. The composition according to claim 1, wherein said extract comprises polyphenol compounds.

4. A method for photoprotecting skin comprising applying an effective amount of the composition of claim 1 to the skin of a subject in need thereof.

* * * * *